United States Patent
Ransbury et al.

(10) Patent No.: US 10,857,352 B2
(45) Date of Patent: Dec. 8, 2020

(54) CATHETER SYSTEM FOR ACUTE NEUROMODULATION

(71) Applicant: Interventional Autonomics Corporation, Chapel Hill, NC (US)

(72) Inventors: Terrance J Ransbury, Chapel Hill, NC (US); Richard S Stack, Chapel Hill, NC (US); William E Sanders, Chapel Hill, NC (US); Stephen C Masson, Raleigh, NC (US)

(73) Assignee: NUXCEL Limited, Dublin (IE)

( * ) Notice: Subject to any disclaimer, the term of this patent is extended or adjusted under 35 U.S.C. 154(b) by 0 days.

(21) Appl. No.: 15/855,991

(22) Filed: Dec. 27, 2017

(65) Prior Publication Data

US 2018/0117305 A1    May 3, 2018

Related U.S. Application Data

(63) Continuation of application No. 14/151,755, filed on Jan. 9, 2014, now Pat. No. 9,884,182, which is a continuation of application No. PCT/US2012/046332, filed on Jul. 11, 2012.

(60) Provisional application No. 61/506,164, filed on Jul. 11, 2011.

(51) Int. Cl.
*A61N 1/05* (2006.01)
*A61N 1/36* (2006.01)
*A61B 5/0215* (2006.01)
*A61N 1/365* (2006.01)

(52) U.S. Cl.
CPC ............ *A61N 1/056* (2013.01); *A61B 5/0215* (2013.01); *A61N 1/3605* (2013.01); *A61N 1/36114* (2013.01); *A61N 1/36564* (2013.01)

(58) Field of Classification Search
USPC ........................................................ 607/116
See application file for complete search history.

(56) References Cited

FOREIGN PATENT DOCUMENTS

WO    WO 2007092330 A1 *  8/2007  ........ A61M 5/14276

* cited by examiner

*Primary Examiner* — Nicole F Lavert

(57) ABSTRACT

A neuromodulation system includes a first therapy element adapted for positioning within a superior vena cava, and a second therapy element adapted for positioning within a pulmonary artery. The first therapy element is carried on a first elongate flexible shaft, and the second therapy element is carried on a second elongate flexible shaft. One of the first and second shafts is slidably received within a lumen of the other of the first and second shafts—so that the second therapy element may be advanced within the body relative to the first therapy element. A stimulator is configured to energize the first therapy element within the first blood vessel to deliver therapy to a first nerve fiber disposed external to the superior vena cava and to energize the second therapy element within the pulmonary artery to deliver sympathetic therapy to a second nerve fiber disposed external to the pulmonary artery. For treatment of heart failure, the first nerve fiber may be a vagus nerve and the second nerve fiber may be a sympathetic nerve fiber.

7 Claims, 4 Drawing Sheets

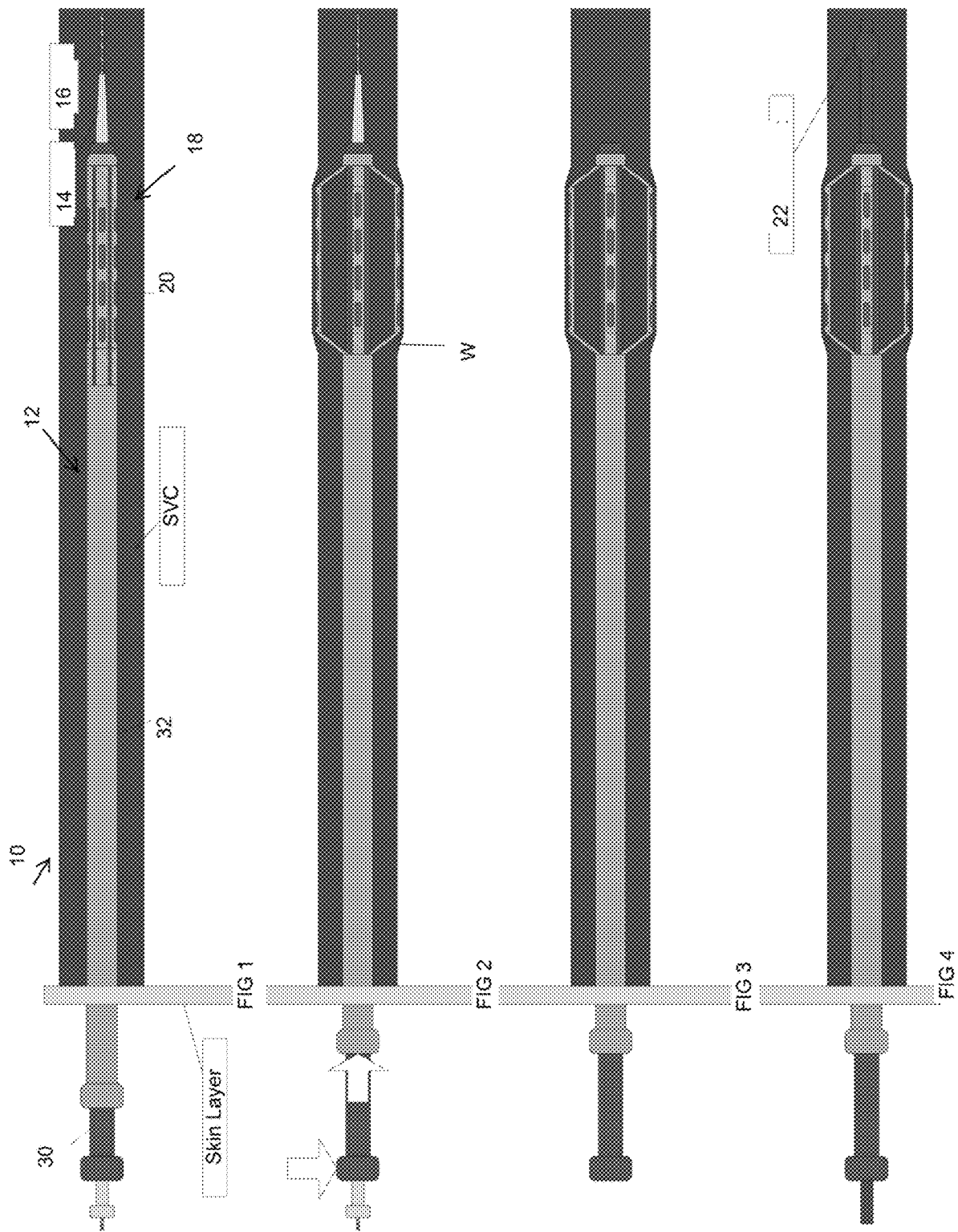

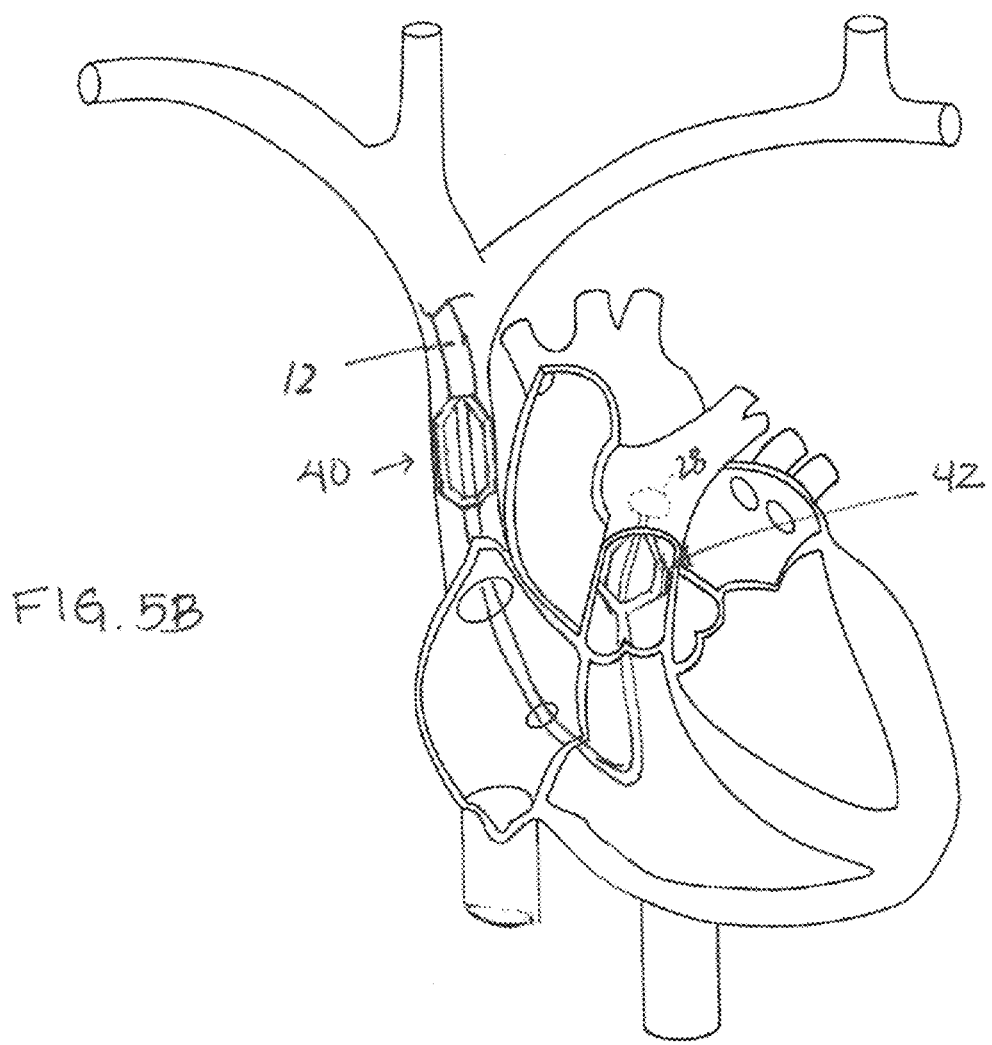

CATHETER SYSTEM FOR ACUTE NEUROMODULATION

PRIORITY

This application is a continuation of U.S. application Ser. No. 14/151,755, filed Jan. 9, 2014, now U.S. Pat. No. 9,884,182, which is a continuation of PCT/US2012/46332 filed 11 Jul. 2012, published as WO 2013/022543 and now expired, which claims the benefit of U.S. Provisional Application No. 61/506,164, filed 11 Jul. 2011, each of which is incorporated herein by reference.

TECHNICAL FIELD OF THE INVENTION

The present application generally relates to systems and methods for acute neuromodulation using stimulation elements disposed within the vasculature.

BACKGROUND

Acute heart failure syndromes (AHFS) are serious conditions resulting in millions of hospitalizations each year. AHFS treatments can include pharmacologic inotrope administration—however side effects of such treatments, including arrhythmias and increased myocardial oxygen demand, can contribute to patient mortality. Additional treatments include administration of diuretics to treat pulmonary edema resulting from AHFS.

The autonomic nervous system includes the parasympathetic nervous system and the sympathetic nervous system. The parasympathetic and sympathetic nervous system have somewhat opposing effects on the cardiovascular system. One function of the parasympathetic nervous system is to slow the heart through action of the vagus nerve. On the other hand, the sympathetic nervous system is associated with increasing the heart rate and increasing the contractility of the heart. The disclosed system and method may be used to augment balance between the sympathetic and parasympathetic systems in AHFS patents so as to lower heart rate, elevate heart rate and/or increase heart contractility.

BRIEF DESCRIPTION OF THE DRAWINGS

FIGS. 1-4 are a sequence of drawings illustrating deployment of a first embodiment of a catheter system, in which:

FIG. 1 shows the system in a blood vessel prior to expansion of the anchoring element;

FIG. 2 is similar to FIG. 1 but shows the anchoring element expanded;

FIG. 3 illustrates the system following removal of the guide wire and dilator, and FIG. 4 is similar to FIG. 3 but shows a Swan-Ganz catheter extending through the lumen of the catheter.

FIG. 5B schematically illustrates positioning of the neuromodulation device of FIG. 5A within the vasculature;

DETAILED DESCRIPTION

Figure 5A:
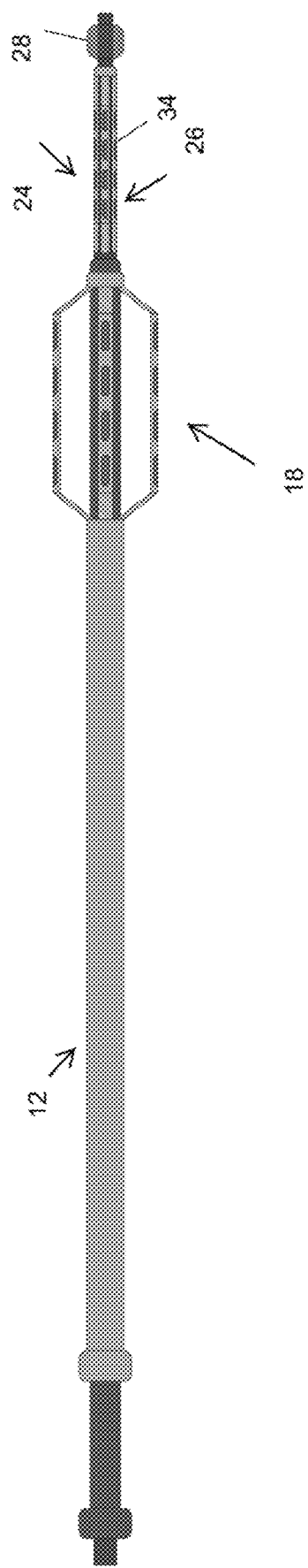
FIG. 5A is similar to FIG. 4 but shows a second neuromodulation device extending through the lumen of the catheter.

The present application discloses a catheter system for neuromodulation. One application of the system is for acute use in treating AHFS through parasympathetic and/or sympathetic neuromodulation. However it should be understood that the system may alternatively be used to treat other conditions, or to maintain autonomic balance at times where the patient's own nervous system could benefit from assistance in maintaining autonomic balance. One example of this latter application is to use the system to maintain autonomic balance while the patient is intubated, is in a coma, or is otherwise experiencing autonomic dysfunction. Other conditions that could be treated with acute neuromodulation include, but are not limited to, acute myocardial infarction, pulmonary embolism, hemorrhage, systemic inflammatory response syndrome (SIRS), sepsis, and post-surgery autonomic dysfunction.

A neuromodulation system for treating AHFS provides therapeutic elements for modulation of parasympathetic and/or sympathetic fibers. In some embodiment, only parasympathetic fibers are stimulated, while in other embodiments parasympathetic and sympathetic fibers are stimulated at the same time and/or at different times to improve autonomic balance in the heart. In preferred embodiments, the therapeutic elements are positioned on one or more catheters positioned in the vasculature of the patient and are energized to modulate nerve fibers positioned outside the vascular walls. Modulation may be carried out to activate and/or inhibit or block activation of target nerve fibers. In the disclosed system, the therapeutic elements are described as electrodes, although it is contemplated that other forms of therapeutic elements (including, but not limited to, ultrasound, thermal, or optical elements) may instead be used.

The parasympathetic and sympathetic fibers may be modulated from the same therapeutic element or element array, or from different elements or element arrays. Elements used to modulate sympathetic fibers may be positioned in the same blood vessels as those used for the parasympathetic fibers, or they may be in different blood vessels. The blood vessel and the target position of the therapeutic elements within a chosen vessel is selected based on the vessel's anatomic location relative to the target fiber so as to position the therapeutic element in close proximity to the target fiber while minimize collateral effects. For example, in the canine model, right sympathetic fibers modulating left ventricular contractility converge at the common pulmonary artery and course in the pulmonary artery nerves. Left sympathetic fibers modulating ventricular contractility are found near the common pulmonary artery, pulmonary artery nerves, and ventral lateral cardiac nerve. In contrast, sympathetic fibers controlling chronotropic and dromotropic functions are found between the superior vena cava (SVC) and aorta, between the common pulmonary artery and the proximal right pulmonary artery, between the left superior pulmonary vein and the right pulmonary artery, and elsewhere. J. L. Ardell et al, *Differential sympathetic regulation of automatic, conductile, and contractile tissue in dog heart*. The anatomy thus allows a therapeutic element to be positioned to selectively stimulate sympathetic fibers controlling ventricular inotropy to increase contractility, while avoiding chronotropic/dromotropic effects so as not to trigger tachycardia.

In human use, modulation of sympathetic fibers may be achieved using a therapeutic element positioned within the pulmonary artery so as to stimulate sympathetic fibers to increase inotropy. Moreover, therapeutic elements could additionally or alternatively be employed to stimulate parasympathetic fibers that lower heart rate. Such fibers may also be activated using intravascular electrodes located in the pulmonary arteries, although in other embodiments vagal or other parasympathetic fibers are modulated using a therapeutic element in the superior vena cava or the internal jugular vein, preferably on the right side.

In some embodiments, combined or alternating modulation of the parasympathetic and sympathetic fibers may be employed to optimize the opposing effects of parasympathetic and sympathetic modulation on heart rate—such that modulation optimizes the ability of the sympathetic system to drive the heart rate and the parasympathetic system to "apply the brakes" to slow the heart when necessary. Sensed or derived hemodynamic parameters may be used by the system to select and implement stimulation parameters, algorithms and/or to identify the therapeutic element(s) to be activated at a given time. Suitable sensed or derived hemodynamic parameters include pulmonary capillary wedge pressure (PCWP), cardiac index, derivations of vascular resistance, heart rate, and blood pressure (arterial). Other parameters may include central venous pressure, CO/CI, and cardiac filling pressures.

FIGS. 1-4 illustrate a first embodiment of a catheter system 10, which includes a treatment catheter 12, a dilator 14, and a guide wire 16. The treatment catheter 12 includes a tubular inner sheath 30 and a tubular outer sheath 32, which are connected at their distal end sections.

The distal end section of the outer sheath includes one or more anchoring elements 18 that are expanded or extended into contact with the surrounding vessel wall so as to anchor the catheter in a desired location. The anchoring element(s) may be an expandable basket or stent-like device, or one or more spline elements as illustrated in the drawings. In the illustrated configuration, these elements are outwardly expandable into contact with the vessel wall W when the outer sheath 32 is pushed distally relative to the inner sheath 30 as illustrated in FIG. 2. Since the inner and outer sheaths are connected at their distal end portions, sliding the outer sheath distally relative to the inner sheath causes the anchoring elements to bow outwardly into contact with the vessel wall as shown. Stimulation electrodes 20 are mounted to or formed on the anchoring element(s) 18, or the anchoring element(s) may themselves be configured to function as electrodes. The electrodes are preferably positioned such that expanding the anchoring elements into contact with the vessel wall places the active surfaces of the electrodes into contact with the vessel wall, allowing energy for neuromodulation to conduct from the electrodes through the vessel wall to target nerve fibers adjacent to the vessel (e.g. in the adjacent extravascular space).

The inner sheath 30 includes a lumen, allowing the catheter 12 to function both as a neuromodulation catheter and an introducer for other medical devices useful for the procedure. Examples include catheters for patient monitoring (e.g. Swan-Ganz), additional electrode catheters or leads for a variety of applications such as mapping target stimulation sites, cardiac pacing, or ablation, or catheters/leads carrying neuromodulation electrodes positionable at a second intravascular site to target additional nerve fibers.

In one method of using the first embodiment, a percutaneous Seldinger technique is used to place the guidewire 16 into the venous vasculature, such as via the femoral vein, internal or external jugular vein, or subclavian vein. The dilator 14, which is preferably preloaded into the lumen of the inner sheath 30, is advanced together with the catheter over the wire and directed to the target blood vessel. The user advances the outer sheath 32 relative to the inner sheath 30 (such as by holding the hub of the inner sheath while pushing the hub of the outer sheath distally as shown in FIG. 2)—causing the anchoring elements 18 to expand into contact with the surrounding vessel wall, thus anchoring the catheter at the target site in the vessel and placing the electrodes 20 into contact with the vessel wall. The relative positions of the inner and outer sheath hubs may be locked using a ratchet or locking mechanism (not shown) to maintain the anchoring elements in the expanded position.

The dilator and wire are removed from the catheter lumen either before or after anchoring of the catheter.

In one embodiment, the target vessel is the superior vena cava, and the catheter 12 is anchored such that energizing the electrodes (or a select group of electrodes within the array) will cause a desired effect (e.g. enhance, augment, inhibit or block signaling) on vagus nerve fibers adjacent to the superior vena cava. Once the electrodes are expanded into contact with the vessel wall, mapping procedures may be carried out as known in the art (measuring the effect of stimulus at various electrode locations) to identify the optimal positions of the electrodes or to identify the best combination of electrodes within the array to energize for the desired response.

Additional medical devices are advanced through the inner sheath lumen as discussed above, such that their distal portions extend from the distal end of the catheter. FIG. 4 shows use of a Swan-Ganz catheter 22 through the inner sheath 30. FIG. 5A shows that a second electrode lead or catheter 24 can be advanced through the lumen of the inner sheath 30. The second electrode lead or catheter may have one or more expandable anchoring elements 26 as discussed above with respect to the catheter 12 (and as shown in FIG. 5A in the unexpanded position), with electrodes 34 mounted to or formed on the anchoring elements 26 as disclosed. The second electrode lead or catheter 24 may include an inflatable balloon 28 on its distal tip as shown, to facilitate advancement of the second electrode lead/catheter 24 to a target site. It may also include sensing functionality, such as the ability to sense pressures including, but not limited to, PCWP. For example, if the second electrode lead/catheter 24 is to be positioned within the pulmonary artery, inflating the balloon within the right ventricle can help the electrode lead/catheter float with the flowing blood into the pulmonary artery in the manner similar to the way in which a Swan-Ganz catheter is positioned. The balloon 28 may be positioned on the second lead/catheter 34 itself, or on an additional catheter extending through a lumen in the lead/catheter 34.

In one exemplary procedure using the FIG. 5A embodiment, the electrodes 20 of the catheter 12 are anchored in the superior vena cava as discussed above for neuromodulating parasympathetic activity of the vagus nerve (to slow the heart, for example), and the electrodes 34 of the second lead/catheter 24 are anchored in the pulmonary artery for directing energy to sympathetic nerves that will enhance heart contractility and/or increase heart rate. Referring to FIG. 5B, in a positioning method according to this embodiment, the catheter is advanced into the superior vena cava and anchoring elements 18 are expanded to position the electrodes 20 against the wall of the SVC, placing the first electrode array 40 in position to stimulate the vagus nerve. Next, the second lead/catheter 24 is further extended from the lumen of the inner sheath 30, and passed or caused to through the right atrium and right ventricle of the heart and into the pulmonary artery using the method described in the prior paragraph or alternative methods. Once in a target position within the pulmonary artery (e.g. pulmonary trunk, or left or right pulmonary artery), the anchoring elements of the second lead/catheter 24 are expanded, positioning the electrodes 34 in apposition with the pulmonary artery wall and thus placing the second electrode array 42 in position to stimulate sympathetic nerves (or, if desired, parasympathetic nerves) in proximity to the pulmonary artery. Pressure may be monitored using pressure transducers on the second lead/catheter, and/or the balloon may be used to monitor pulmonary capillary wedge pressure.

Figure 6:
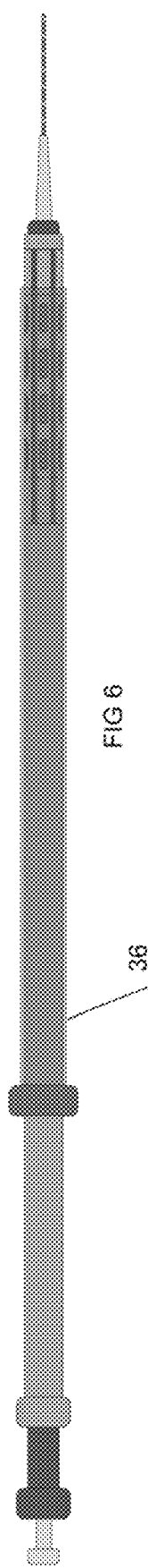
FIGS. 6 and 7 are similar to FIGS. 1 and 4 but show a second alternative configuration for expanding the anchoring element.
Figure 7:
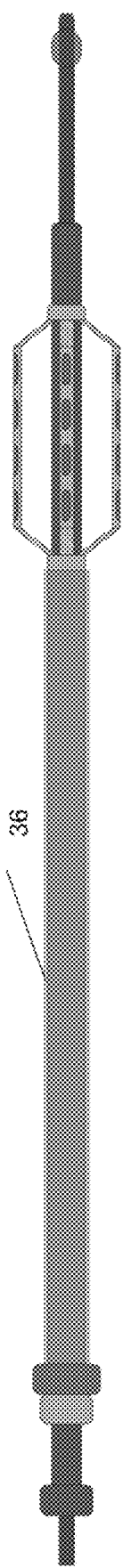

In a slightly modified version of the FIG. 1-4 embodiment, deployment of the anchoring elements 18 is accomplished by pulling the inner sheath 30 proximally relative to the outer sheath 32. FIGS. 6-7 show yet another configuration utilizing anchoring elements that are self-expandable upon retraction of an outer sleeve 36 (shown compressing the anchoring elements in FIG. 6 and withdrawn from them in FIG. 7) that maintains the anchoring element(s) in a compressed position until it is retracted. In still other embodiment, pull cables may be tensioned from the proximal end of the catheter to expand the anchoring elements.

The disclosed catheter system may be coupled to external pulse generator used to energize the electrodes using stimulation parameters selected to capture the target nerve fibers and to achieve the desired neuromodulation. Feedback to the pulse generator is provided by one or more diagnostic sensors, including feedback from sensors mounted on or extending through the lumen of the catheter-introducer. The simulation parameters may be determined or adjusted in response to information sensed by the sensors and/or derived from sensor feedback. Suitable sensed or derived hemodynamic parameters include pulmonary capillary wedge pressure (PCWP), cardiac index, derivations of vascular resistance, heart rate, blood pressure (arterial). Other parameters may include central venous pressure, CO/CI, and cardiac filling pressures.

We claim:

1. A neuromodulation method for treating a patient, comprising:
    positioning a first therapy element in a first blood vessel, the first therapy element carried on a first elongate shaft, wherein the elongate shaft includes
        an outer sheath having a distal portion with an outer sheath distal tip, an anchoring element integral with the outer sheath and radially expandable from the distal portion of the outer sheath from a streamlined to an expanded position in response to axial compression of the outer sheath, the outer sheath further including a plurality of electrodes on the anchoring element, and a proximal portion proximal portion, and
        an inner sheath slidably disposed within the outer sheath and including a distal portion with an inner sheath distal tip, and a proximal portion, the inner and outer sheath having distal portions fixed to one another such that relative longitudinal positions of the outer sheath distal tip and the inner sheath distal tip on the elongate shaft remain constant when relative longitudinal positions of the proximal portions of the inner and outer sheaths are changed,
    moving the electrodes into contact with an interior wall of the first blood vessel by causing relative longitudinal movement of proximal portions of the inner and outer sheaths in opposite directions while the distal portions remain fixed to one another, said relative longitudinal movement of the proximal portions causing axial compression of the outer sheath, thereby moving the expandable anchoring element from the streamlined position to the expanded position;
    positioning a second therapy element in a second blood vessel different from the first blood vessel, the second therapy element carried on a second shaft, wherein one of the first and second shafts is slidably received within a lumen of the other of the first and second shafts; and
    activating a stimulator to (a) energize the first therapy element within the first blood vessel to deliver therapy to a first nerve fiber disposed external to the first blood vessel and (b) energize the second therapy element within the second blood vessel to deliver sympathetic therapy to a second nerve fiber disposed external to the first blood vessel.

2. The method of claim 1, further including the step of controlling the stimulator to energize the first and second therapy elements in response to said sensed heart rate and/or blood pressure.

3. The method of claim 1, wherein positioning the second therapy element includes at least partially expanding the second therapy element into contact with surrounding walls of the second blood vessel.

4. The method of claim 1, wherein positioning the second therapy element in the second blood vessel comprises positioning the second therapy element within a pulmonary artery.

5. The method of claim 4, wherein positioning the second therapy element includes inflating an expandable balloon coupled to the second therapy element when the first therapy element is retained in the first blood vessel such that expansion of the balloon causes the second therapy element to be carried by blood flow from the heart to the pulmonary artery.

6. The method of claim 4, wherein positioning the first therapy element includes positioning the first therapy element within a superior vena cava.

7. The method of claim 1 wherein the anchoring element includes elongate splines, and wherein in the step of moving the electrodes, the axial compression of the outer sheath causes the splines to bow outwardly to move the anchoring element to the expanded position.

* * * * *